United States Patent [19]
Green et al.

[11] Patent Number: 5,674,231
[45] Date of Patent: Oct. 7, 1997

[54] APPARATUS AND METHOD FOR VASCULAR HOLE CLOSURE

[75] Inventors: David T. Green, Westport; Scott E. Manzo, Shelton; Peter W. J. Hinchliffe, New Haven, all of Conn.

[73] Assignee: United States Surgical Corporation, Norwalk, Conn.

[21] Appl. No.: 545,974

[22] Filed: Oct. 20, 1995

[51] Int. Cl.⁶ .................................................. A61B 17/10
[52] U.S. Cl. .......................................... 606/142; 606/139
[58] Field of Search .................................. 606/142, 139, 606/140, 141, 135, 143; 227/901, 175.1

[56] References Cited

U.S. PATENT DOCUMENTS

| | | |
|---|---|---|
| Re. 34,866 | 2/1995 | Kensey et al. . |
| 2,513,771 | 7/1950 | Williams . |
| 4,532,134 | 7/1985 | Malette et al. . |
| 4,744,364 | 5/1988 | Kensey . |
| 4,852,568 | 8/1989 | Kensey . |
| 4,854,320 | 8/1989 | Dew et al. . |
| 4,929,240 | 5/1990 | Kirsch et al. . |
| 5,021,059 | 6/1991 | Kensey et al. . |
| 5,030,226 | 7/1991 | Green et al. . |
| 5,053,046 | 10/1991 | Janese . |
| 5,061,274 | 10/1991 | Kensey . |
| 5,100,420 | 3/1992 | Green et al. . |
| 5,108,421 | 4/1992 | Fowler . |
| 5,129,882 | 7/1992 | Weldon et al. . |
| 5,156,608 | 10/1992 | Troidl et al. ................. 606/142 |
| 5,156,613 | 10/1992 | Sawyer . |
| 5,192,300 | 3/1993 | Fowler . |
| 5,192,301 | 3/1993 | Kamiya et al. . |
| 5,192,302 | 3/1993 | Kensey et al. . |
| 5,207,670 | 5/1993 | Sinofsky . |
| 5,217,473 | 6/1993 | Yoon ........................... 606/157 |
| 5,221,259 | 6/1993 | Weldon et al. . |
| 5,222,974 | 6/1993 | Kensey et al. . |
| 5,226,908 | 7/1993 | Yoon ........................... 606/141 |
| 5,254,105 | 10/1993 | Haaga . |
| 5,275,616 | 1/1994 | Fowler . |
| 5,282,827 | 2/1994 | Kensey et al. . |
| 5,290,310 | 3/1994 | Makower et al. . |
| 5,292,332 | 3/1994 | Lee . |
| 5,310,407 | 5/1994 | Casale . |
| 5,342,393 | 8/1994 | Stack . |
| 5,370,660 | 12/1994 | Weinstein et al. . |
| 5,383,896 | 1/1995 | Gershony et al. . |
| 5,383,897 | 1/1995 | Wholey . |
| 5,383,899 | 1/1995 | Hammerslag . |
| 5,391,183 | 2/1995 | Janzen et al. . |
| 5,411,520 | 5/1995 | Nash et al. . |
| 5,413,571 | 5/1995 | Katsaros et al. . |
| 5,415,657 | 5/1995 | Taymor-Luria . |
| 5,417,699 | 5/1995 | Klein et al. . |
| 5,437,631 | 8/1995 | Janzen . |
| 5,441,517 | 8/1995 | Kensey et al. . |
| 5,443,477 | 8/1995 | Marin et al. . |
| 5,443,481 | 8/1995 | Lee . |
| 5,447,502 | 9/1995 | Haaga . |

*Primary Examiner*—Michael Buiz
*Assistant Examiner*—Tina T. D. Pham

[57] ABSTRACT

An apparatus and method are disclosed for applying a surgical clip to an exterior wall of a blood vessel to at least partially close a hole formed therein. The apparatus includes a handle portion, an elongated body extending distally from the handle portion and dimensioned to extend through a hole in the wall of a blood vessel, and a collapsible locator associated with a distal end portion of the elongated body and mounted for movement between a collapsed position and an expanded deployed position. The locator is adapted to expand within an interior lumen of the blood vessel to maintain the distal end portion of the elongated body in a desired location with respect to the hole in blood vessel wall such that a surgical clip releasably supported adjacent the distal end portion of the elongated body can be applied to the exterior wall of the blood vessel to close the hole formed therein.

34 Claims, 13 Drawing Sheets

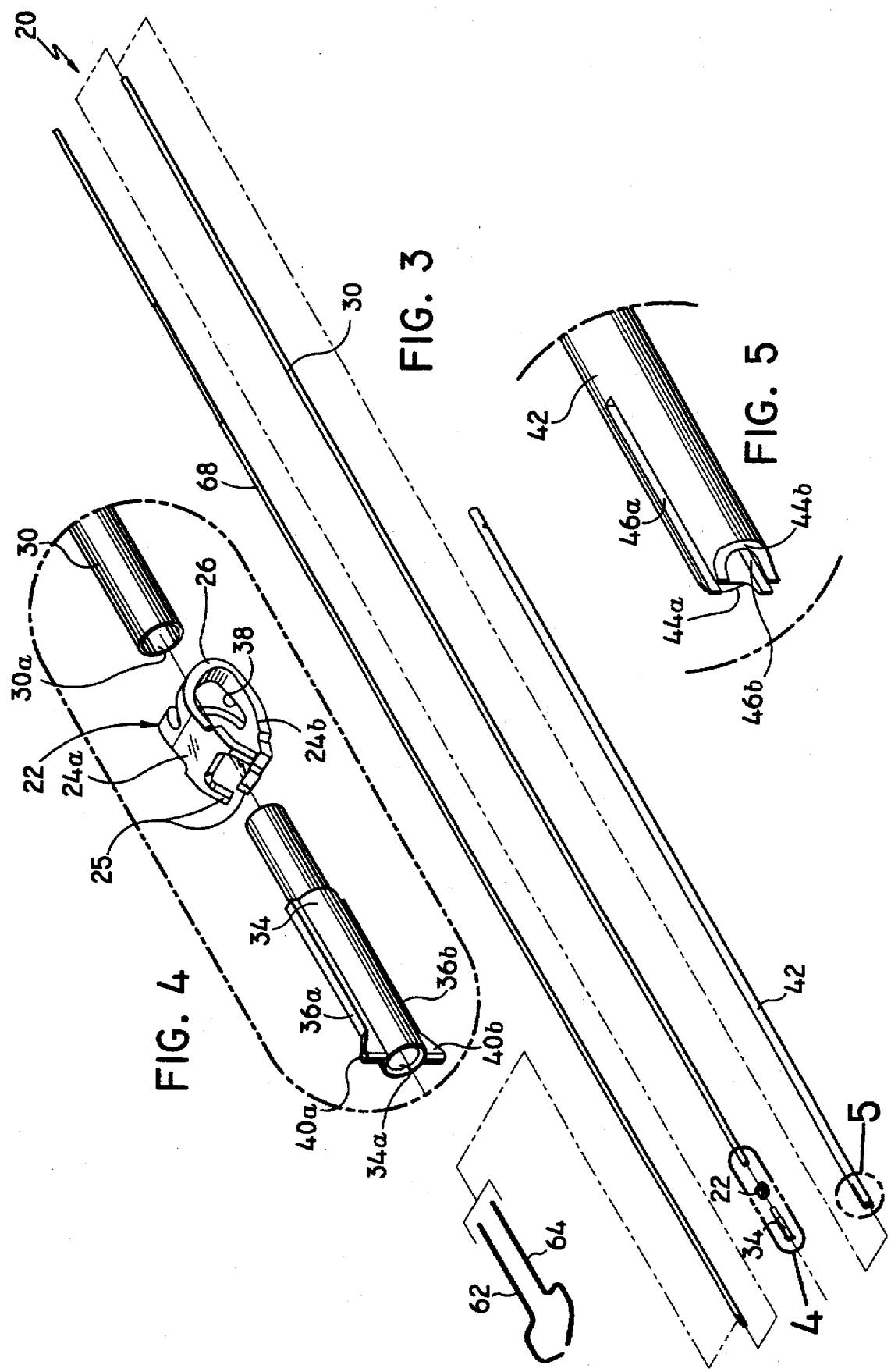

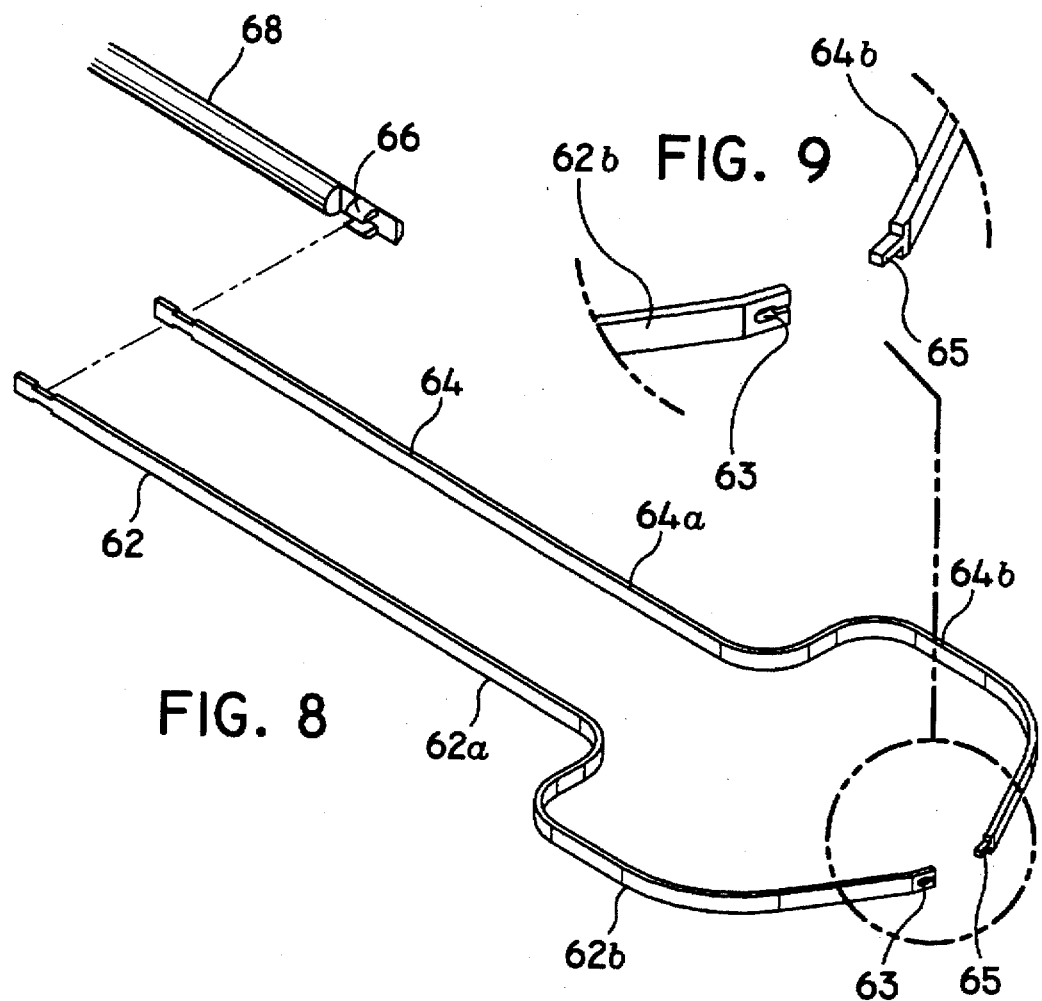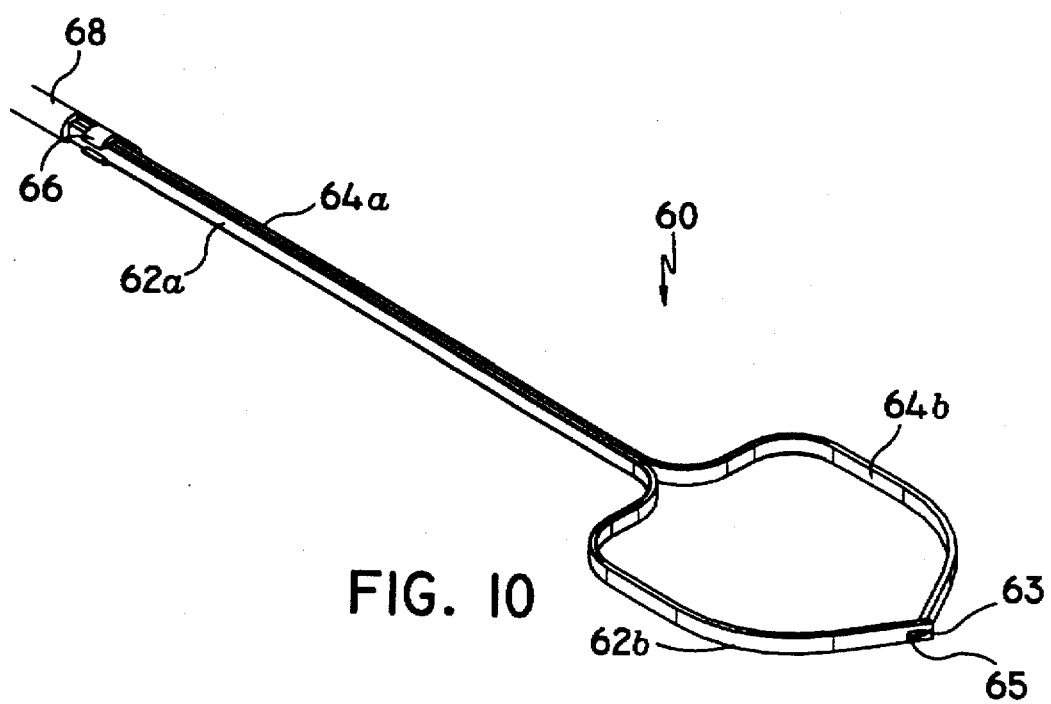

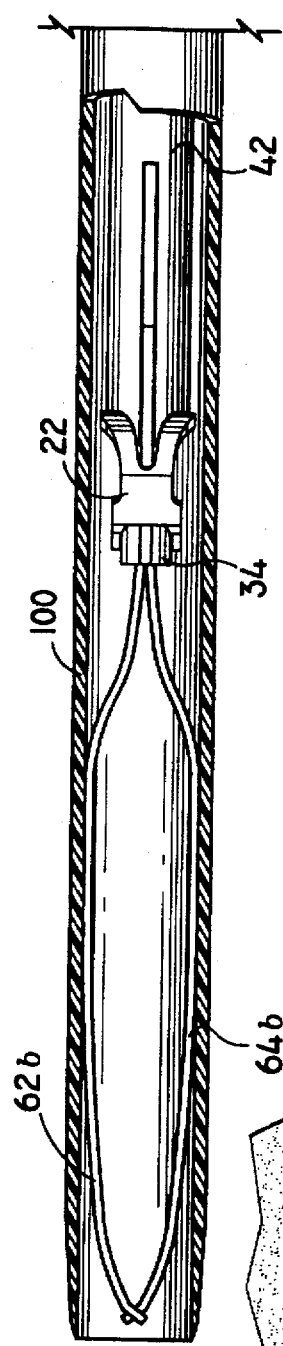
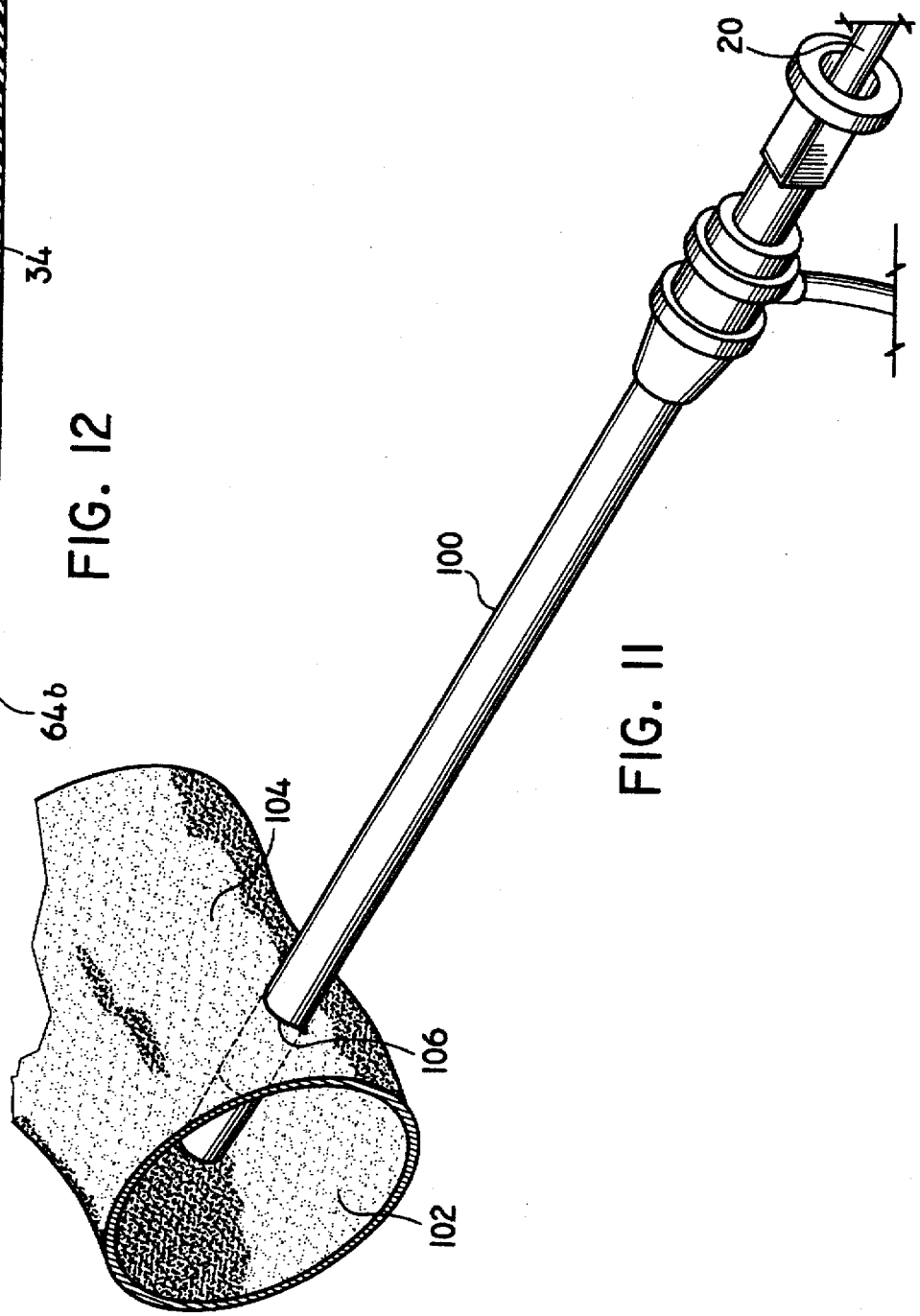
FIG. 12
FIG. 11

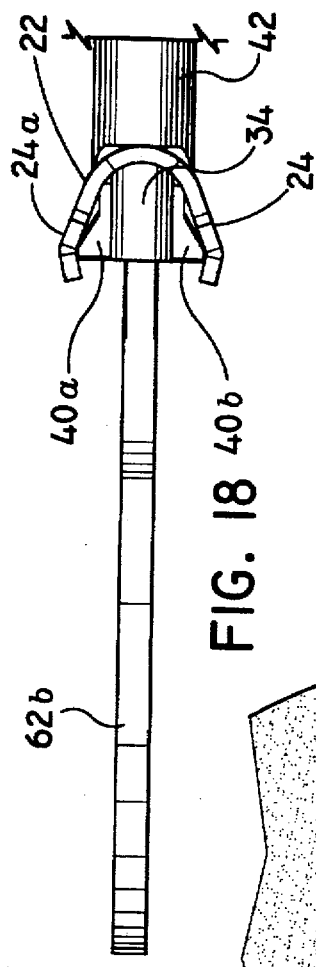
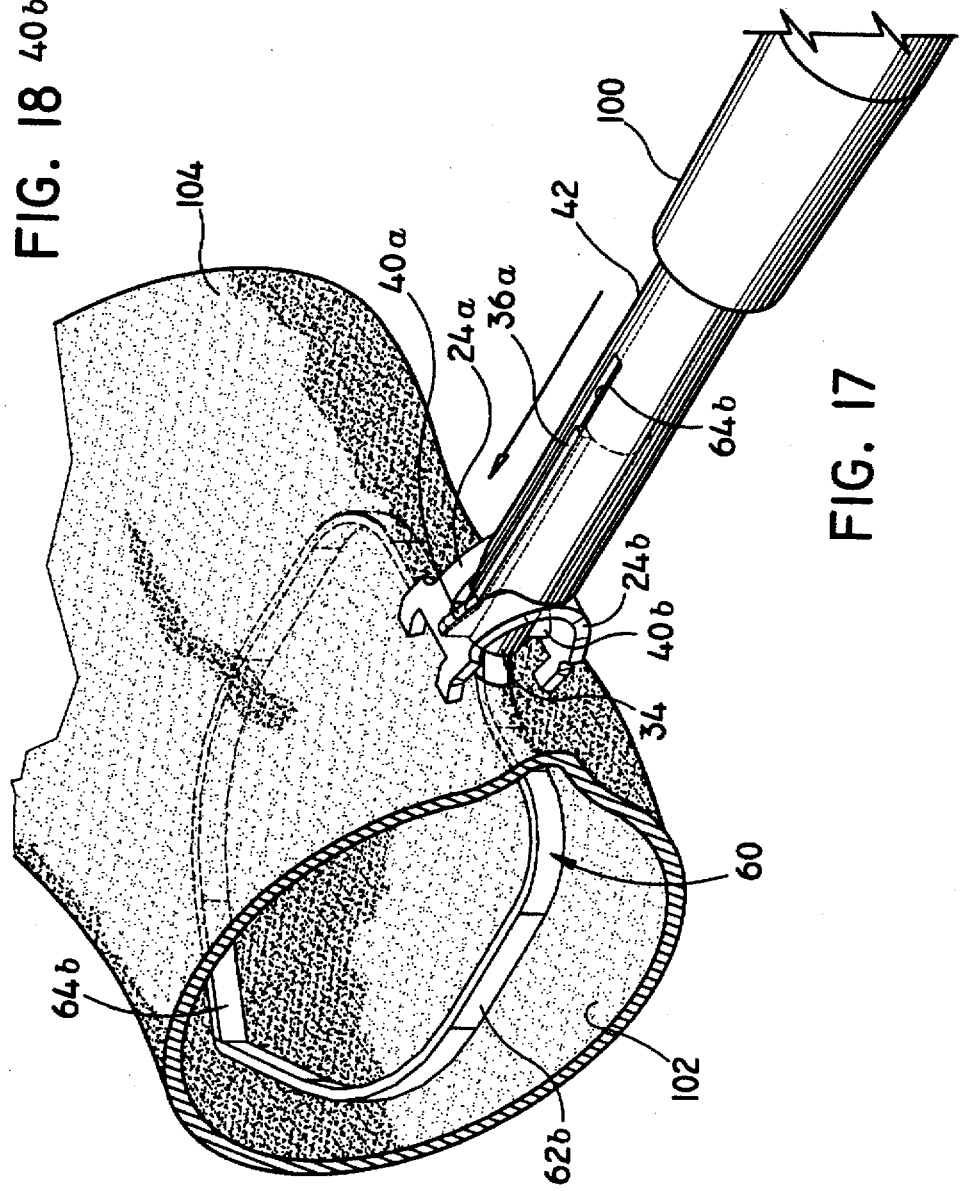

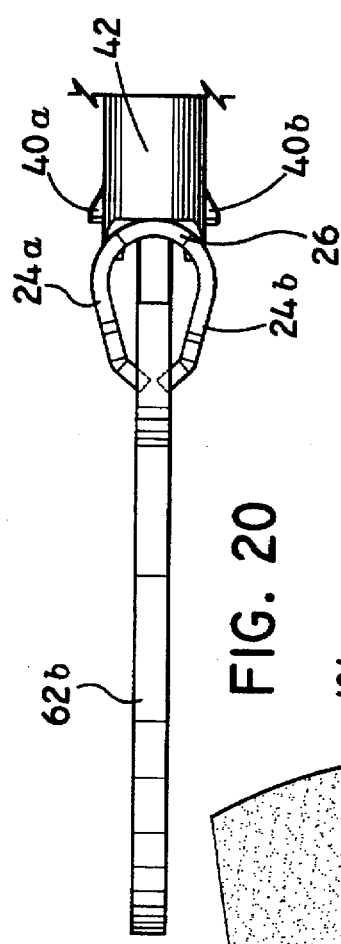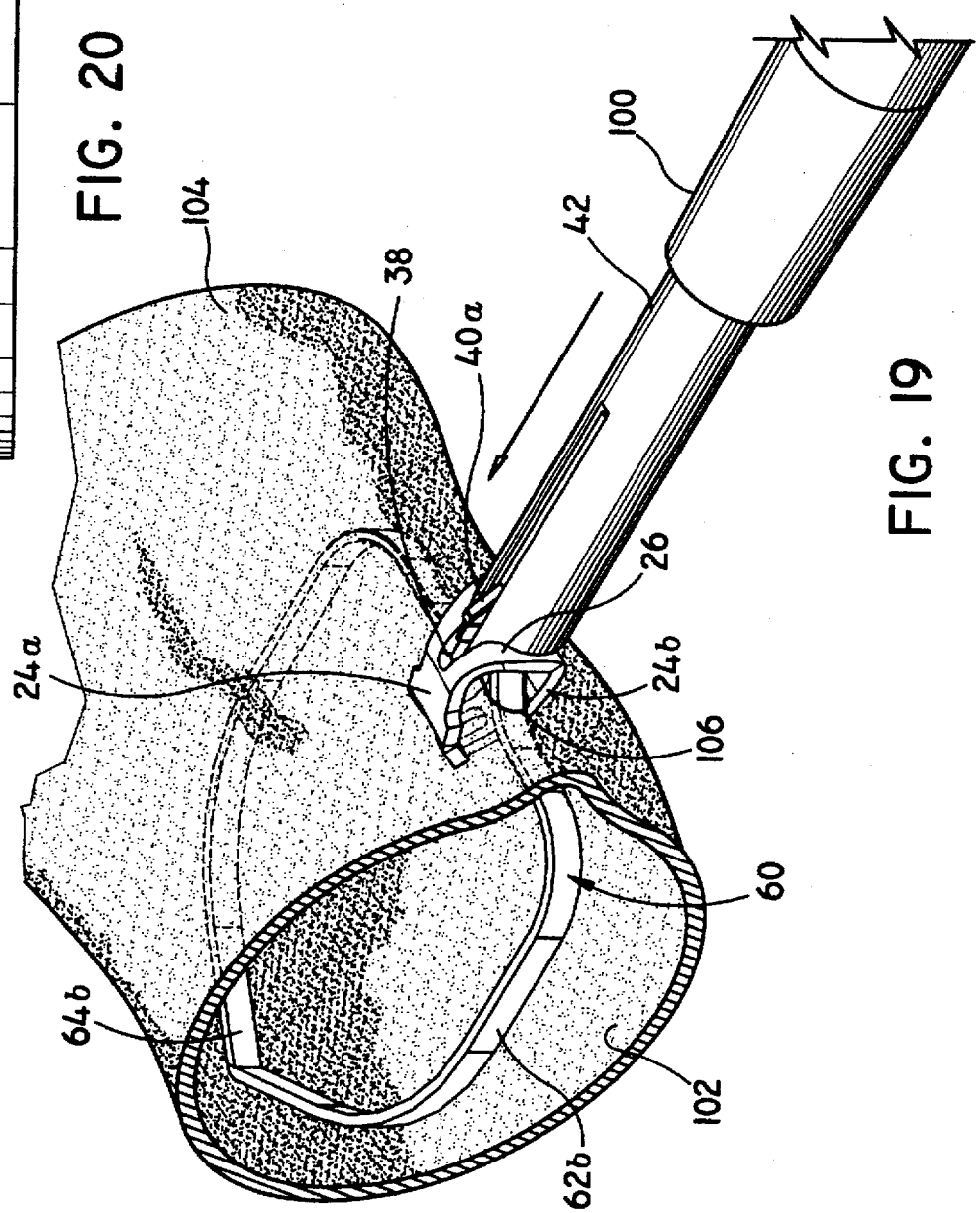
FIG. 20
FIG. 19

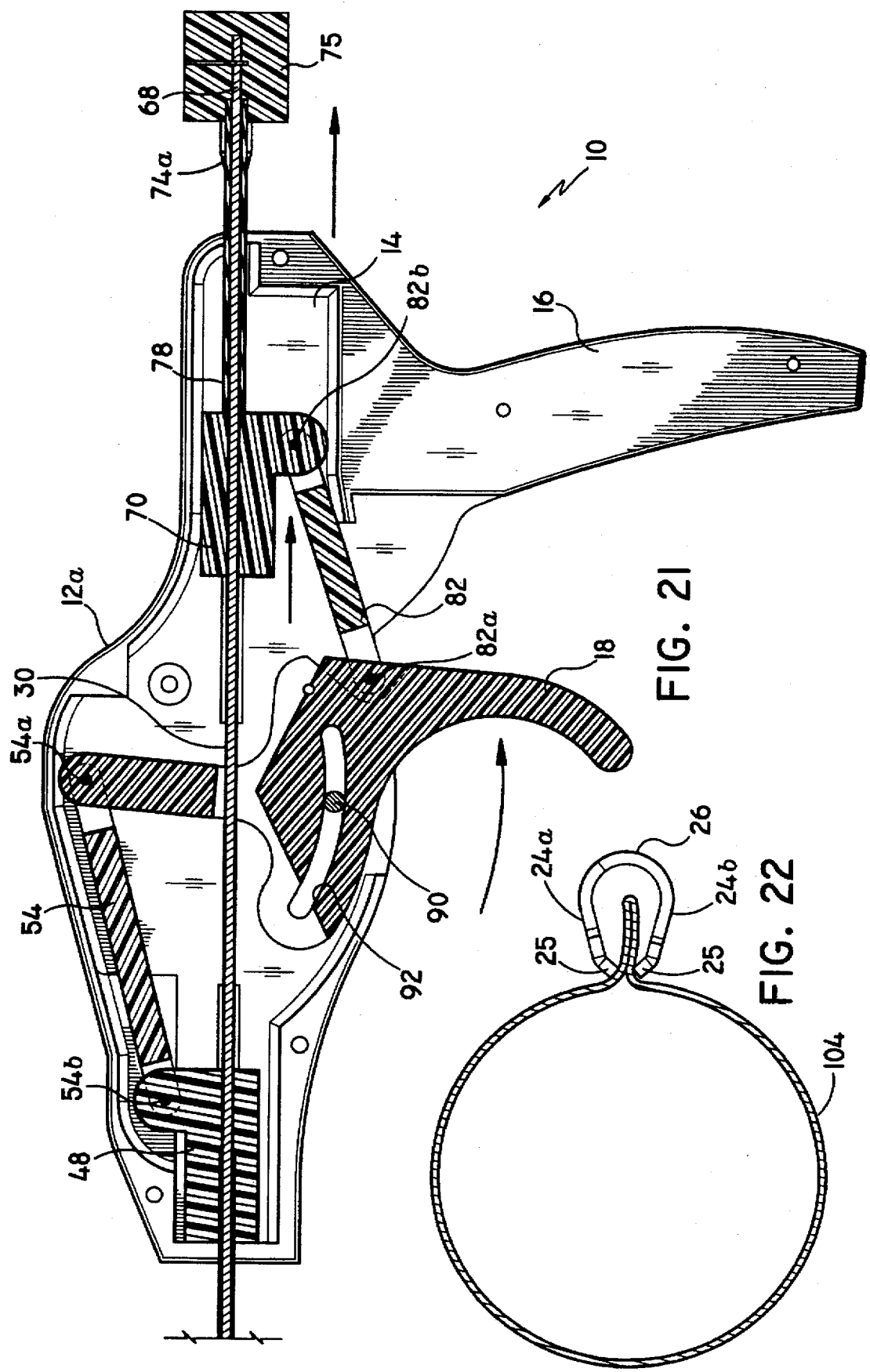

`5,674,231`

APPARATUS AND METHOD FOR VASCULAR HOLE CLOSURE

BACKGROUND

1. Technical Field

The present disclosure relates to an apparatus and method for closing a hole or puncture in a blood vessel, and more particularly, to an apparatus for applying a surgical clip to a blood vessel to close a hole formed therein during an intravascular catheterization procedure.

2. Background of Related Art

When performing a catheterization procedure such as, for example, an angiography or angioplasty, a sharpened hollow needle is first percutaneously introduced into the vascular system. A guide wire is then inserted through the hollow needle and into the lumen of a selected blood vessel. Subsequently, the needle is removed and a dilator and/or introducer is fed into the vessel along the guide wire. The guide wire is then removed and a suitable catheter is fed through the lumen of the introducer and advanced through the vascular system until the working end thereof is positioned at the operating site. At the conclusion of the catheterization procedure, the catheter is withdrawn, and subsequently, the dilator and/or introducer is also removed from the wound.

At this point in the procedure, the vessel puncture must be sealed in order to stem the flow of blood therethrough. Because it is often common practice to administer a blood thinning agent to the patient prior to the catheterization procedures, stemming the blood flow can be troublesome. A common method of healing the wound is to maintain external pressure over the vessel until the puncture naturally seals. This method of puncture closure typically takes about thirty minutes, with the length of time usually being greater if the patient is hypertensive or anti-coagulated. When hand pressure is utilized, it can be uncomfortable for the patient and can use costly professional time on the part of the hospital staff. Other pressure application techniques, such as pressure bandages, sandbags or clamps, have been employed, but these devices also require the patient to remain motionless for an extended period of time and the patient must be closely monitored to ensure their effectiveness.

Other devices have been disclosed which plug or otherwise provide an obstruction in the area of the puncture. See, for example, U.S. Pat. Nos. 4,852,568 and 4,890,612, wherein a collagen plug is disposed in the blood vessel opening. When the plug is exposed to body fluids, it swells to create a block for the wound in the vessel wall. A potential problem of plugs introduced into the vessel is that particles may break off and float downstream to the point where they may lodge in a smaller vessel, causing an infarct to occur. Collagen material also acts as a nidus for platelet aggregation and, therefore, can cause intraluminal deposition of hemostatic agent, thereby creating the possibility of a thrombosis at the puncture sight. Other plug-like devices are disclosed, for example, in U.S. Pat. Nos. 5,342,393; 5,370,660; and 5,411,520.

Surgical clips and clip appliers are known and have been used in vascular surgery, particularly to join severed vessels. See, for example, U.S. Pat. No. 4,929,240 (Kirsch, et al.). The clips disclosed in the '240 Patent provide an advantage over suturing by decreasing the likelihood of clotting and vascular damage, particularly in micro-vascular repair procedures. While vascular clips have been successfully used in surgery, the surgical procedures in which the clips are used typically allow the surgeon to view the area to be clipped. In catheter puncture repair procedures, however, the wound is generally not visible, making proper clip application, if attempted, difficult.

Therefore, there is a need for surgical techniques and apparatus suitable for closing punctures in blood vessels, particularly those created during catheterization procedures. This need requires a reliable hemostasis of the puncture in a quick and efficient manner. It would also be advantageous to close the puncture without disposing any foreign substances within the vessel, thereby preventing the likelihood of introducing foreign matter into the circulatory system. The technique also needs to be performed without directly viewing the punctured vessel.

SUMMARY

The subject application is directed to an apparatus and method for applying a surgical clip to an exterior wall of a blood vessel to at least partially close a hole formed therein during a catheterization procedure. The apparatus includes a handle portion, an elongated body extending distally from the handle portion and dimensioned to extend through a hole in the wall of a blood vessel, and a collapsible locator operatively associated with the elongated body and mounted for movement between a collapsed retracted position disposed within a distal end portion of the elongated body and an expanded deployed position extending from the distal end portion of the elongated body. The locator is preferably adapted and configured to expand within an interior lumen of the blood vessel in the deployed position to maintain the distal end portion of the elongated body in a desired location with respect to the hole in blood vessel wall. A surgical clip is releasably supported adjacent the distal end portion of the elongated body which is configured for application to the exterior wall of the blood vessel to at least partially close the hole formed therein when the locator is substantially in the deployed position.

Preferably, the surgical clip has a pair of opposed clip legs connected by a bail portion, and the bail portion has an aperture provided therein to accommodate movement of the locator from the deployed position to the retracted position upon application of the clip to the exterior wall of the blood vessel. A control rod extends from the handle portion through the elongated body and is mounted for movement between a proximal position and a distal position to effectuate the movement of the collapsible locator between the retracted position and the deployed position, and a control knob is operatively mounted to a proximal end of the control rod to facilitate the longitudinal movement thereof. The control knob preferably includes means for releasably engaging the handle portion when the collapsible locator is disposed in the deployed position.

In a preferred embodiment of the subject apparatus, the elongated body includes an outer tubular member mounted for axial movement with respect to the handle portion between a proximal position and a distal position, and structure is provided adjacent a distal end of the elongated body for releasably supporting the surgical clip. A pair of diametrically opposed camming ramps are preferably formed adjacent a distal end of the elongated body, distal of the clip support structure, to cause the opposed legs of the surgical clip to move between a closed position and an open position in response to longitudinal movement of the outer tubular member from the distal position toward the proximal position.

An actuation handle is operatively associated with the handle portion of the surgical apparatus and is mounted for manipulation through an actuating stroke. Preferably, movement of the actuation handle through a first segment of the actuating stroke causes the outer tubular member to move from the proximal position to the distal position, and movement of the actuation handle through a second segment of the actuating stroke causes the actuation rod to move from the distal position to the proximal position. In addition, movement of the actuation handle through the second segment of the actuating stroke releases the control knob from an engaged position.

In a preferred embodiment of the surgical apparatus disclosed herein, distal and proximal actuating members are supported within the handle portion and are operatively connected to the actuation handle. Preferably, a first control link connects the distal actuating member to the actuation handle and second control link connects the proximal actuating member to the actuation handle. The distal actuating member is also connected to a proximal end of the outer tubular member, and the proximal actuating member is also connected to a release tube which is dimensioned to interact with the control knob upon movement of the actuation handle through the second segment of the actuating stroke.

The method disclosed herein includes the steps of taking an elongated body having a surgical clip supported adjacent a distal end portion thereof, extending the elongated body through the hole in the blood vessel such that at least a distal end portion thereof projects into an interior lumen of the blood vessel, and deploying a locator from the distal end portion of the elongated body into the interior lumen of the blood vessel to maintain the elongated body in a desired position with respect to the hole in the wall of the blood vessel. The method further includes the steps of applying the surgical clip to the exterior wall of the blood vessel to at least partially close the hole therein, and retracting the locator from the interior lumen of the blood vessel.

In a preferred embodiment of the method, the step of applying the surgical clip includes the step advancing the surgical clip in a distal direction from a proximal support position on the elongated body, and the step of moving the surgical clip between open and closed positions. The step of deploying the locator includes the step of moving the locator from a collapsed position within the distal end position of the elongated body to an expanded position extending from the distal end portion of the body. Preferably, the step of withdrawing the locator is concomitant with the step of applying the surgical clip to the exterior wall of the blood vessel.

Further features of the surgical apparatus and method of the subject application will become more readily apparent to those skilled in the art from the following detailed description of the apparatus and method taken in conjunction with the drawings.

BRIEF DESCRIPTION OF THE DRAWINGS

Various embodiments of the surgical apparatus and method of the subject application will be described hereinbelow with reference to the drawings wherein:

FIG. 3 is an exploded perspective view of the elongated body of the surgical apparatus of FIG. 1 with the components thereof separated for ease of illustration;

FIG. 4 is an enlarged perspective view of the distal end portion of the elongated body of FIG. 3 illustrating the surgical clip and clip support structure associated therewith;

FIG. 5 is an enlarged perspective view of the distal end portion of the clip advancement tube of the elongated body illustrated in FIG. 3;

FIG. 8 is an exploded perspective view of the locator and the distal end portion of the control rod to which the locator is mounted;

FIG. 9 is an enlarged perspective view of the coupling area of the locator illustrated in FIG. 8;

FIG. 10 is a perspective view of the locator in an expanded condition mounted to the distal end of the control rod;

FIG. 11 is a perspective view of a cannula extending through a hole in the wall of a blood vessel with the elongated body of the surgical apparatus of FIG. 1 extended therethrough;

FIG. 12 is an enlarged perspective view of the locator extended from the distal end portion of the surgical apparatus of FIG. 1 and collapsed within the cannula;

FIG. 17 is a perspective view of the distal end portion of the elongated body of the surgical apparatus of FIG. 1 illustrating the clip advancement tube advanced distally to cause the surgical clip to move to an open position;

FIG. 18 is a side-elevational view corresponding to FIG. 17 and illustrating the surgical clip in an open position;

FIG. 19 is a perspective view of the distal end portion of the elongated body of the surgical apparatus of FIG. 1 illustrating the clip advancement tube advanced to a distalmost position to cause the surgical clip to move to a closed position;

FIG. 20 is a side elevational view corresponding to FIG. 19 and illustrating the surgical clip in a closed position;

FIG. 21 is a side elevational view in cross-section of the handle portion of the surgical apparatus of FIG. 1 illustrating the relative orientation of the components associated therewith in positions corresponding to the locator being withdrawn to a retracted position; and FIG. 22 is a side elevational view of the surgical clip applied to the exterior wall of the blood vessel to close the hole formed therein.

DETAILED DESCRIPTION OF PREFERRED EMBODIMENTS

Figures 1, 2:
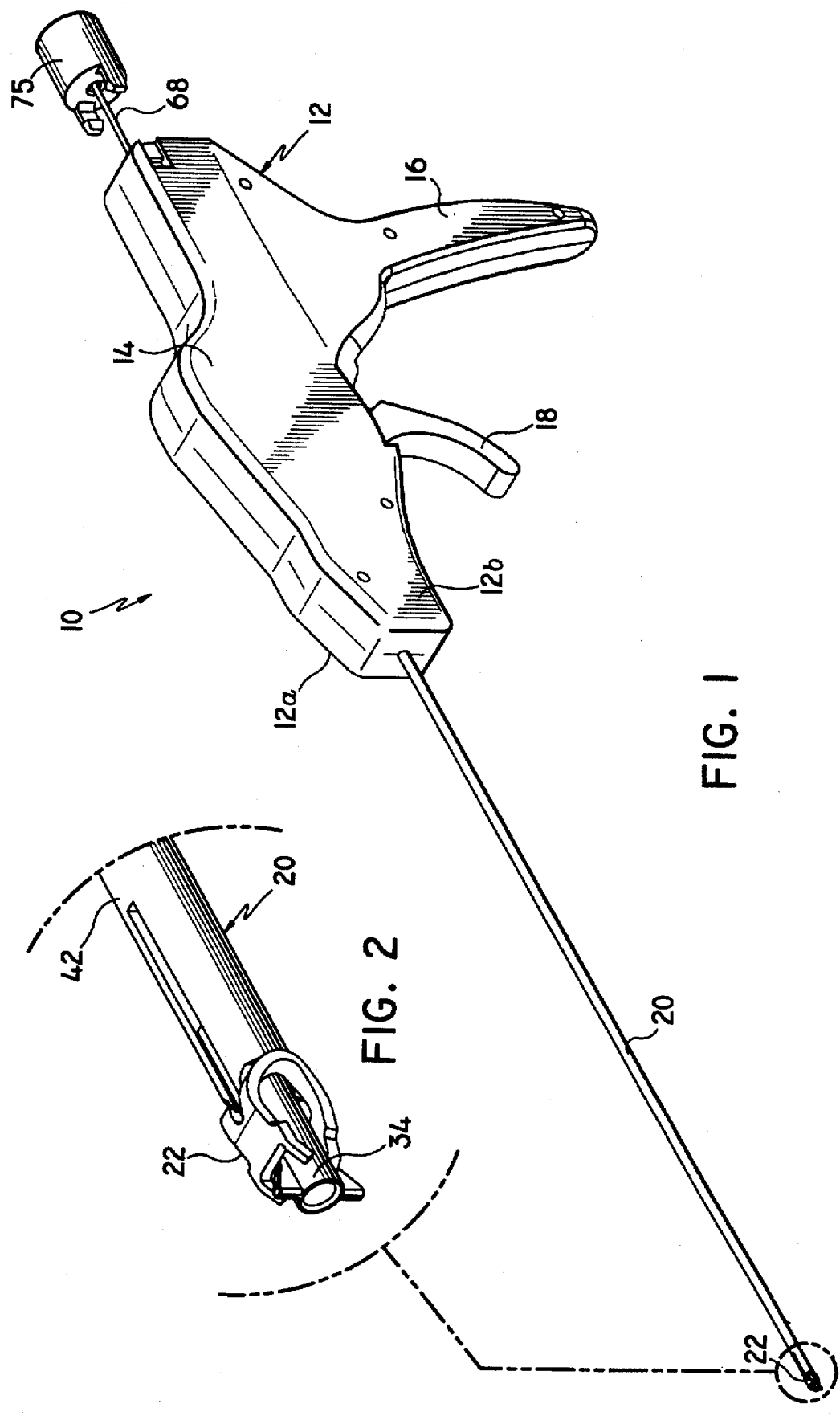
FIG. 1 is a perspective view of a surgical apparatus constructed in accordance with a preferred embodiment of the subject invention in a pre-operative condition.
FIG. 2 is an enlarged perspective view of the distal end portion of the surgical apparatus of FIG. 1 illustrating the surgical clip releasably supported thereon.

In the drawings and in the description which follows, the term "proximal", as is traditional, will refer to the end of the apparatus which is closest to the operator, while the term "distal" will refer to the end of the apparatus which is furthest from the operator.

Referring now to the drawings wherein like reference numerals identify similar structural elements disclosed herein, there is illustrated in FIG. 1 a surgical apparatus constructed in accordance with a preferred embodiment of the subject application and designated generally be reference numeral 10. Surgical apparatus 10 is adapted and configured to apply a surgical clip to the exterior wall of a blood vessel to at least partially close a hole formed therein during a catheterization procedure, such as, for example, an angioplasty or angiography procedure.

Referring to FIG. 1, surgical apparatus 10 includes a handle assembly 12 consisting of right and left housing sections 12a and 12b which together define an elongated barrel portion 14, a stationary handle 16 depending from barrel portion 14, and a pivoting actuation handle or trigger 18 mounted for movement with respect to stationary handle 16. An elongated body 20 extends distally from the barrel portion 14 of handle assembly 12, and a surgical clip 22 is releasably supported on a distal end portion of elongated body 20, as illustrated in FIG. 2. As best seen in FIG. 4, surgical clip 22 includes a pair of opposed clip legs 24a and 24b connected to one another by a bail portion 26. Each clip leg is provided with a pair of tissue engagement projections 25 for securely engaging the exterior wall of the blood vessel to which it is applied (see FIG. 22). Clip legs 24a and 24b are normally biased into a closed position resulting from the overall configuration of surgical clip 22 and the material from which the clip is constructed. The material of construction may be selected from a group consisting of biocompatible materials, including, for example, stainless steel, titanium, and tantalum. Other materials of construction such as bio-absorbable polymers are also envisioned.

Referring to FIG. 3, the elongated body 20 of surgical apparatus 10 includes a main support shaft 30 having an elongated bore 30a extending therethrough. Support shaft 30 extends through the barrel portion 14 of handle assembly 10 and is mounted adjacent a proximal end thereof in a conventional manner. A clip support fixture 34 is mounted in axial bore 30a adjacent the distal end of support shaft 30. As best seen in FIG. 4, support fixture 34 is configured to releasably support surgical clip 22 and includes a pair of diametrically opposed rails 36a and 36b dimensioned to interact with a crescent shaped aperture 38 defined in the bail portion 26 of surgical clip 22. Rails 36a and 36b terminate in distally extending camming ramps 40a and 40b, respectively, which effectuate movement of clip legs 24a and 24b between closed and open positions as surgical clip 22 is advanced in a distal direction during a hole closing procedure.

Advancement of surgical clip 22 in a distal direction relative to camming ramps 40a and 40b is accomplished through the axial translation of an elongated pusher tube 42. Pusher tube 42 is mounted coaxial with support shaft 30 and is configured to translate with respect thereto in response to manipulation of actuation handle 18 to drive surgical clip 22 distally. As best seen in FIG. 5, spaced apart arcuate engagement fingers 44a and 44b project distally from pusher tube 42 to engage the crescent spaced aperture 38 defined in the bail portion 26 of surgical clip 22. Diametrically opposed elongate slots 46a and 46b are formed in the distal portion of pusher tube 42 to accommodate rails 36a and 36b during the distal translation of the pusher tube with respect to support shaft 30.

Figure 6:
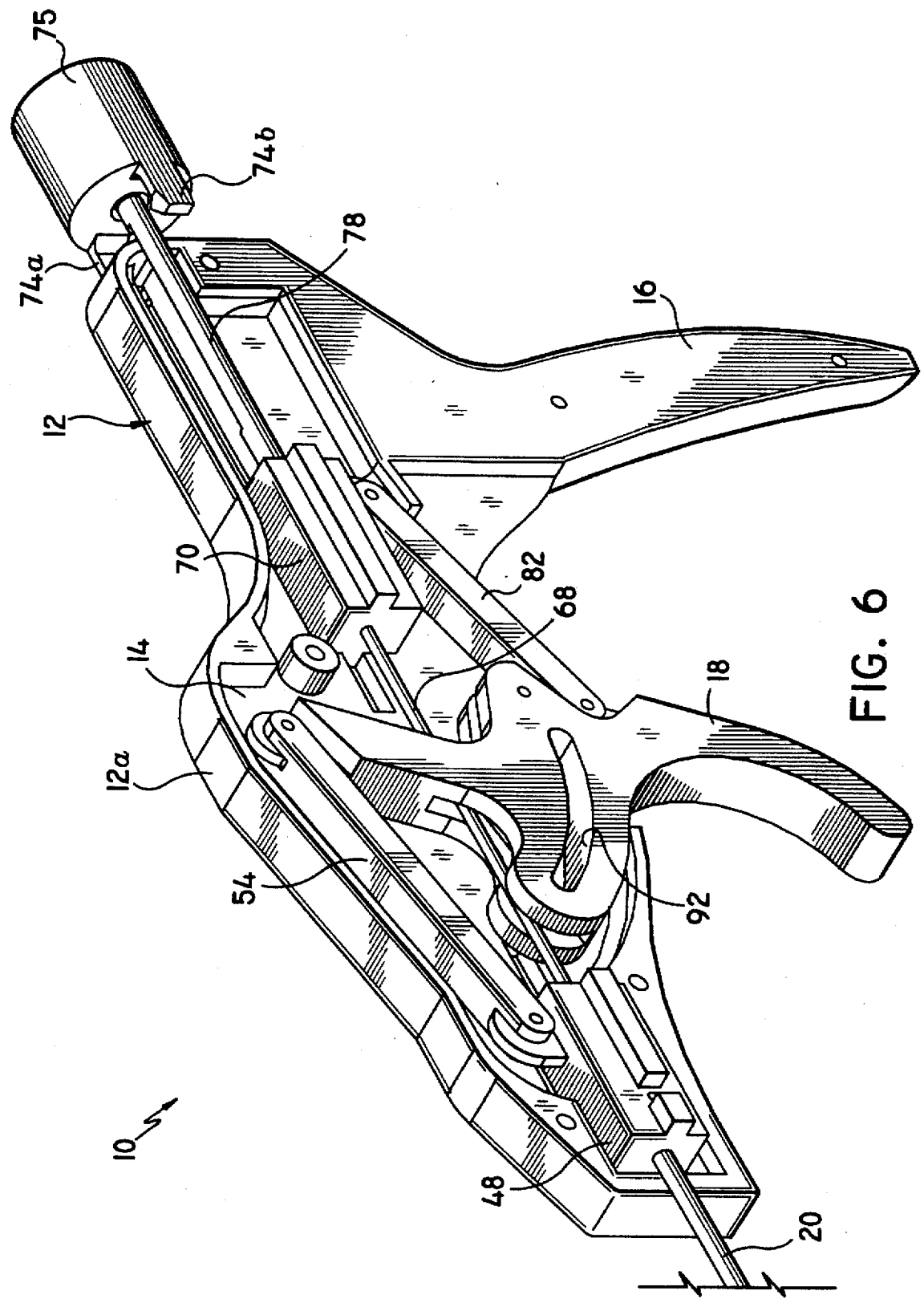
FIG. 6 is a perspective view of the handle portion of the surgical apparatus of FIG. 1 with the left housing section removed to illustrate the internal components housed therein.
Figure 7:
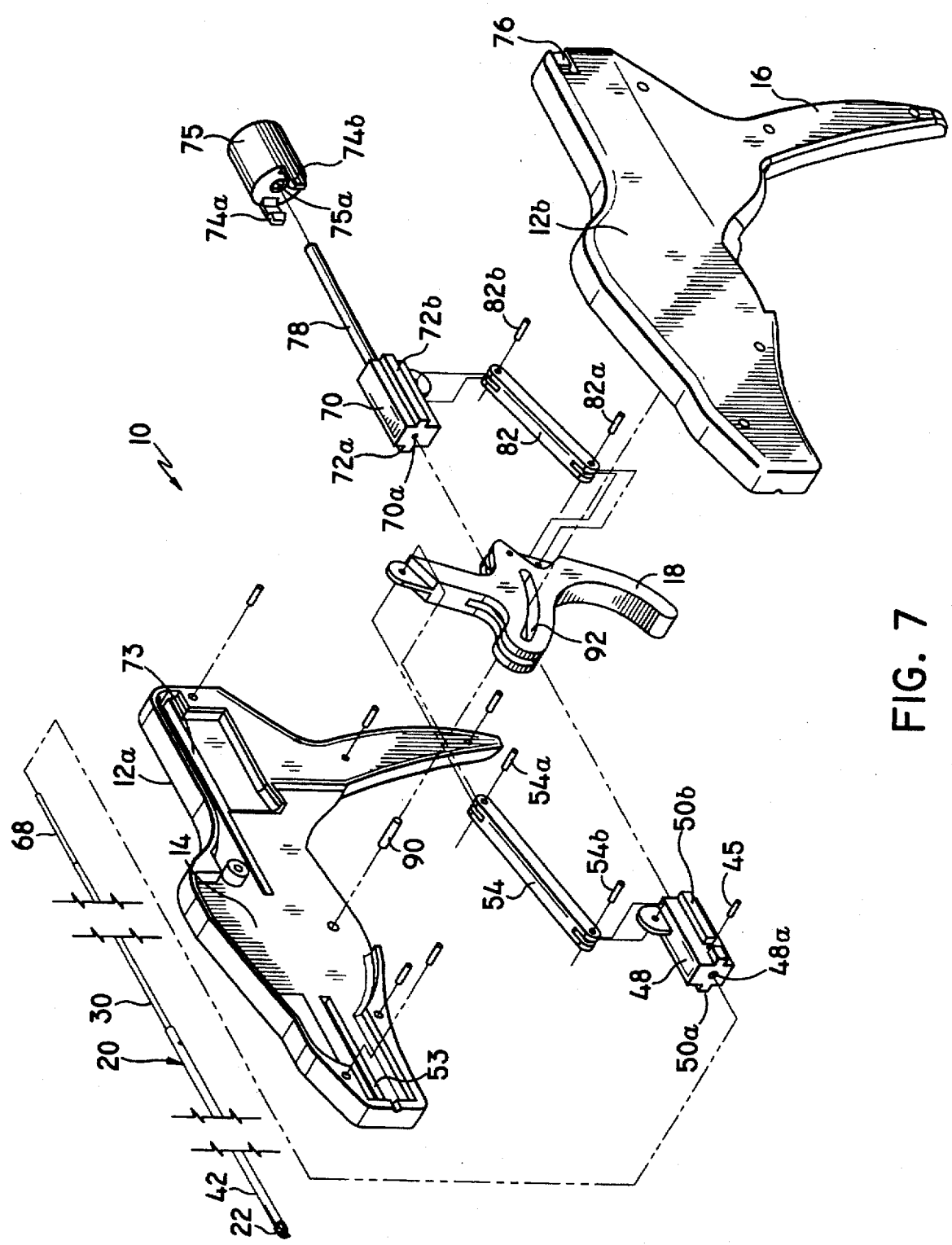
FIG. 7 is an exploded perspective view of the handle portion shown in FIG. 6 with the components thereof separated for ease of illustration.

Referring now to FIGS. 6 and 7, a set pin 45 fixedly connects the proximal end of pusher tube 42 to a distal actuation block 48 which is housed within the barrel portion 14 of handle assembly 12. Actuation block 48 includes opposed lateral guide ribs 50a and 50b which translate within opposed guide slots formed in the interior surfaces of right and left housing sections 12a and 12b, i.e., guide slot 53. A coupling link 54 connects distal actuation block 48 to actuation handle 18 such that manipulation of actuation handle 18 causes actuation block 48 to translate distally, urging pusher tube 42 in a distal direction. Coupling pins 54a and 54b pivotally connect coupling link 54 to actuation block 48 and actuation handle 18.

Referring now to FIGS. 8–10, surgical apparatus 10 also includes a locator 60 in the form of a collapsible loop or ring adapted and configured to maintain the distal end portion of elongated body 20 in a desired position with respect to the hole in the wall of a blood vessel during a hole closing procedure. Locator 60 includes a pair of locator arms 62 and 64 which are constructed from a resilient material that preferably displays shape memory characteristics, such as, for example, a material or alloy consisting of a composition of nickel and titanium. Locator arms 62 and 64 include elongate proximal extension portions 62a and 64a, respectively, and arcuate expansion portions 62b and 64b, respectively. As best seen in FIG. 9, the terminal end of arcuate expansion portion 62b includes an engagement notch 63 for receiving and retaining a complementary engagement finger 65 formed at the terminal end of arcuate expansion portion 64b. When engaged and situated in a relaxed unstressed condition, resilient expansion portions 62b and 64b form an endless loop-like structure. As best seen in FIG. 8, when assembled, the proximal ends of extension portions 62a and 64a are approximated and secured to a coupling flange 66 which is provided at the distal end of an elongated control rod 68 which facilitates movement of locator 60 with respect to support tube 30 during a hole closing procedure.

Figure 13:
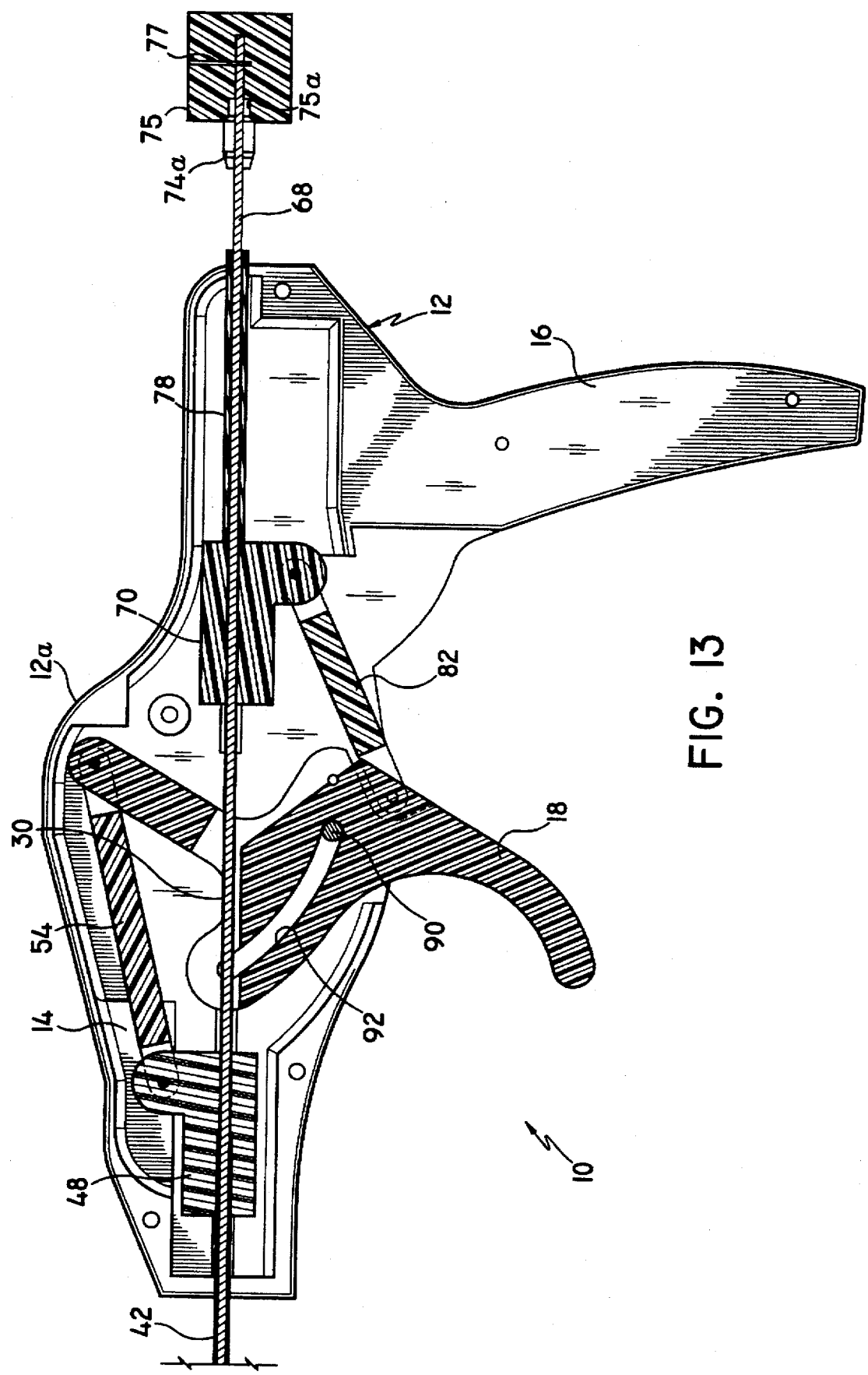
FIG. 13 is a side elevational view in cross-section of the handle portion of the surgical apparatus of FIG. 1 illustrating the relative orientation of the internal components associated therewith in a pre-operative condition.

Referring again to FIGS. 6 and 7, the elongated control rod 68 extends through the axial bore 30a of support tube 30, into the barrel portion 14 of handle assembly 12, through the axial bores 48a and 70a of distal and proximal actuation blocks 48 and 70, out of the proximal end of barrel portion 14, and into the axial bore 75a of a cylindrical control knob 75 operatively associated with handle assembly 12. The proximal end of control rod 68 is fixedly maintained within axial bore 75a of control knob 75 by a fastener 77 (see FIG. 13). Control knob 75 facilitates the longitudinal translation of control rod 68 between proximal and distal positions, and hence the movement of locator 60 from a collapsed (stressed) position disposed within the axial bore 34a of support fixture 34 to a deployed (unstressed) position extending from the distal end of support fixture 34. Control knob 75 includes a pair of engagement tabs 74a and 74b for releasably engaging a pair of complementary retention notches formed on the exterior of housing sections 12a and 12b, i.e., retention notch 76, when locator 60 is disposed in a deployed position.

With continuing reference to FIGS. 6 and 7, an elongated release tube 78 extends proximally from the proximal actuation block 70 to interact with, and effect the disengagement of control knob 75 upon manipulation of actuation handle 18. More particularly, proximal actuation block 70, which includes guide ribs 72a and 72b that translate within opposed guide slots formed in housing sections 12a and 12b, i.e., guide slot 73, is connected to actuation handle 18 by a coupling link 82. Coupling pins 82a and 82b pivotably connect coupling link 82 to actuation block 70 and actuation handle 18. Thus, manipulation of actuation handle 18 causes actuation block 70 to translate in a proximal direction, whereupon release tube 78 enters the axial bore 75a of control knob 75 and urges the control knob proximally to disengage tabs 74a and 74b. As discussed in further detail hereinbelow, the distal and proximal actuation blocks 48 and 70 are connected to actuation handle 18 in such a manner so that control knob 75 will not be released until pusher tube 42 has been advanced to its distal-most position.

Figure 14:
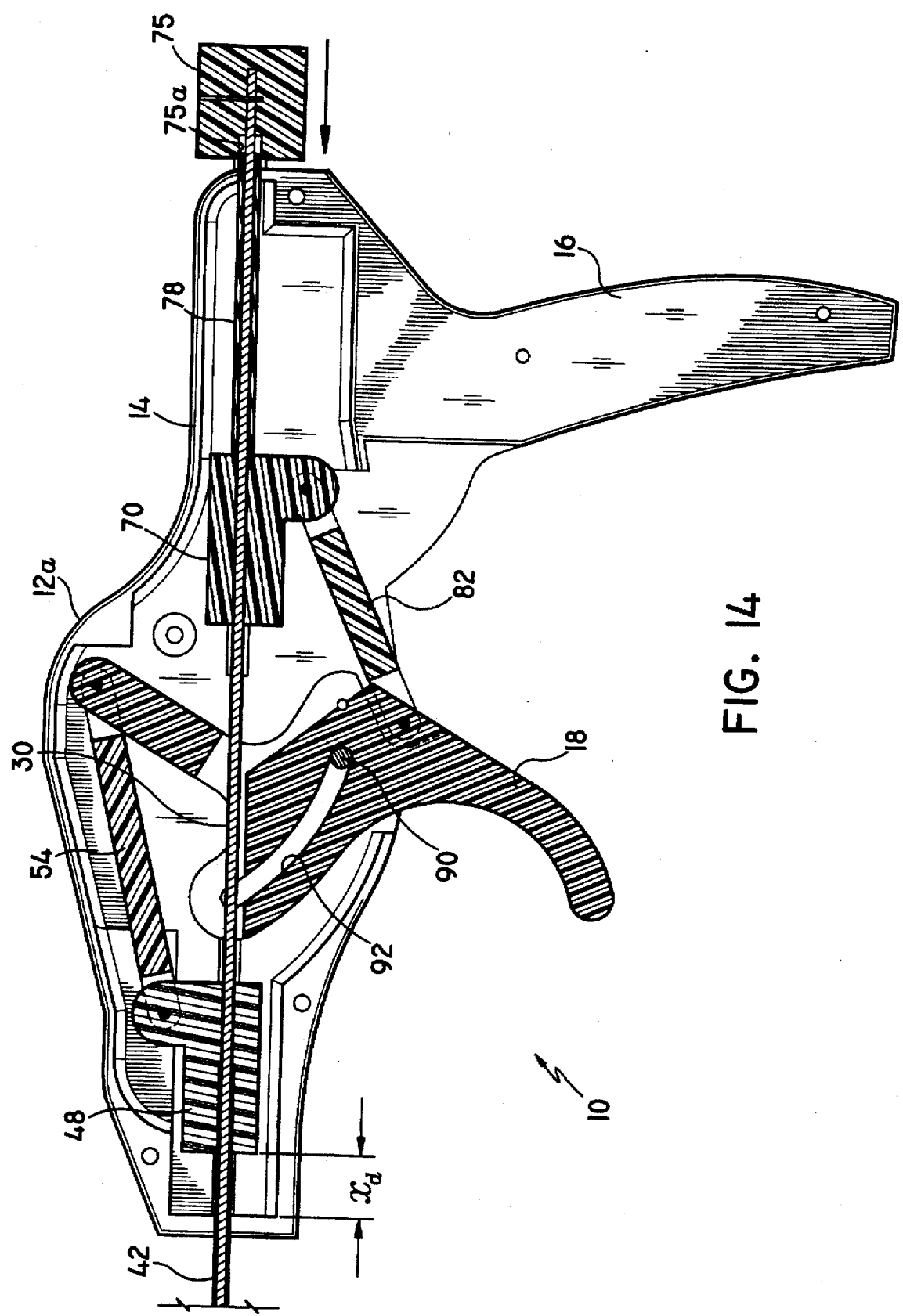
FIG. 14 is a side-elevational view in cross-section of the handle portion of the surgical apparatus of FIG. 1 illustrating the relative orientation of the internal components associated therewith in a condition corresponding to the locator being disposed in a deployed position.

Referring now to FIG. 11, in use, the elongated body 20 of surgical apparatus 10 is introduced into the interior lumen 102 of blood vessel 104 through a conventional cannula 100 which had previously been extended through the hole 106 formed in the wall of blood vessel 104 during the catheterization procedure. Thereupon, locator 60 is moved distally through the translation of control knob 75 from its proximal-most position illustrated in FIG. 13 to its distal-most position illustrated in FIG. 14. Moreover, locator 60 is advanced from its proximal-most position disposed within the axial bore 34a of clip support fixture 34 to its distal-most position extending from the distal end of clip support fixture 34. At such a time, the arcuate expansion portions 62b and 64b of locator arms 62 and 64 remain in a collapsed (stressed) condition restrained within the interior lumen of cannula 100, as best seen in FIG. 12. When control knob 75 is in its proximal-most position shown in FIG. 14, engagement tabs 74a and 74b are releasably engaged to the proximal end of barrel portion 14, thereby securing the longitudinal orientation of control rod 68 and locator 60.

Figure 15:
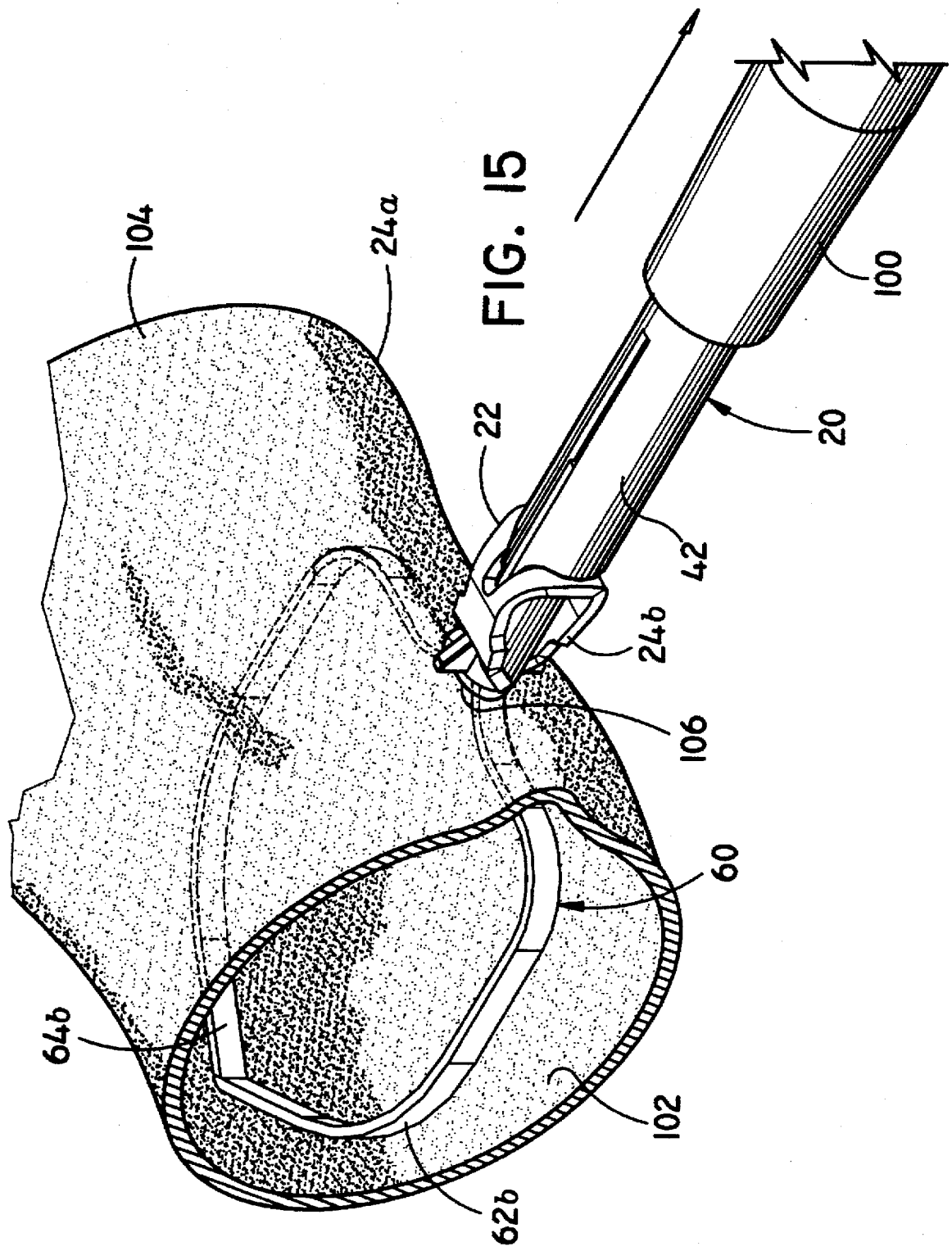
FIG. 15 is a perspective view of a distal end portion of the elongated body of the surgical apparatus of FIG. 1 illustrating the locator disposed in a deployed position within the interior lumen of a blood vessel.

Referring now to FIG. 15, after locator 60 is moved into its distal-most position, cannula 100 is withdrawn in a proximal direction with respect to elongated body 20 to a retracted position. Consequently, the arcuate expansion portions 62b and 64b of locator arms 62 and 64 move into their deployed (unstressed) positions, forming the loop-like structure which maintains the distal end portion of elongated body 20 in a desired position with respect to the hole 106 in the wall of blood vessel 104. In this deployed position, the geometric plane defined by locator 60 is oriented parallel to the elongation of blood vessel 104. Accordingly, the opposed clip legs 24a and 24b of surgical clip 22 extend in a direction which is perpendicular to the elongation of blood vessel 104.

Once locator 60 is deployed, the clip application portion of the vascular hole closure procedure may commence. To apply surgical clip 22 to the exterior wall of blood vessel 104 to at least partially close the hole 106 formed therein, actuation handle 18 is initially moved through the first segment of an actuation stroke, with guide pin 90 serving as the pivot point for actuation handle 18. During this time, actuation handle 18 causes the distal actuation block 48 to translate from its proximal-most position illustrated in FIG. 14 to its distal-most position illustrated in FIG. 16 through a distance "$x_d$" within the barrel portion 14 of handle assembly 12. As a result, pusher tube 42 is driven distally, urging surgical clip 22 in a distal direction.

Initially, during the distal advancement of surgical clip 22, the opposed clip legs 24a and 24b of surgical clip 22 are moved to an open position as the clip translates with respect to camming ramps 40a and 40b, as illustrated in FIGS. 17 and 18. Subsequently, as actuation block 48 approaches its distal-most position within barrel portion 14, pusher tube 42 advances surgical clip 22 passed camming ramps 40a and 40b so that clip legs 24a and 24b return to a closed portion, as illustrated in FIGS. 19 and 20. More specifically, when camming ramps 40a and 40b meet the crescent shaped aperture 38 in the bail portion 26 of surgical 22, clip legs 24a and 24b return to their normally biased closed position.

Figure 16:
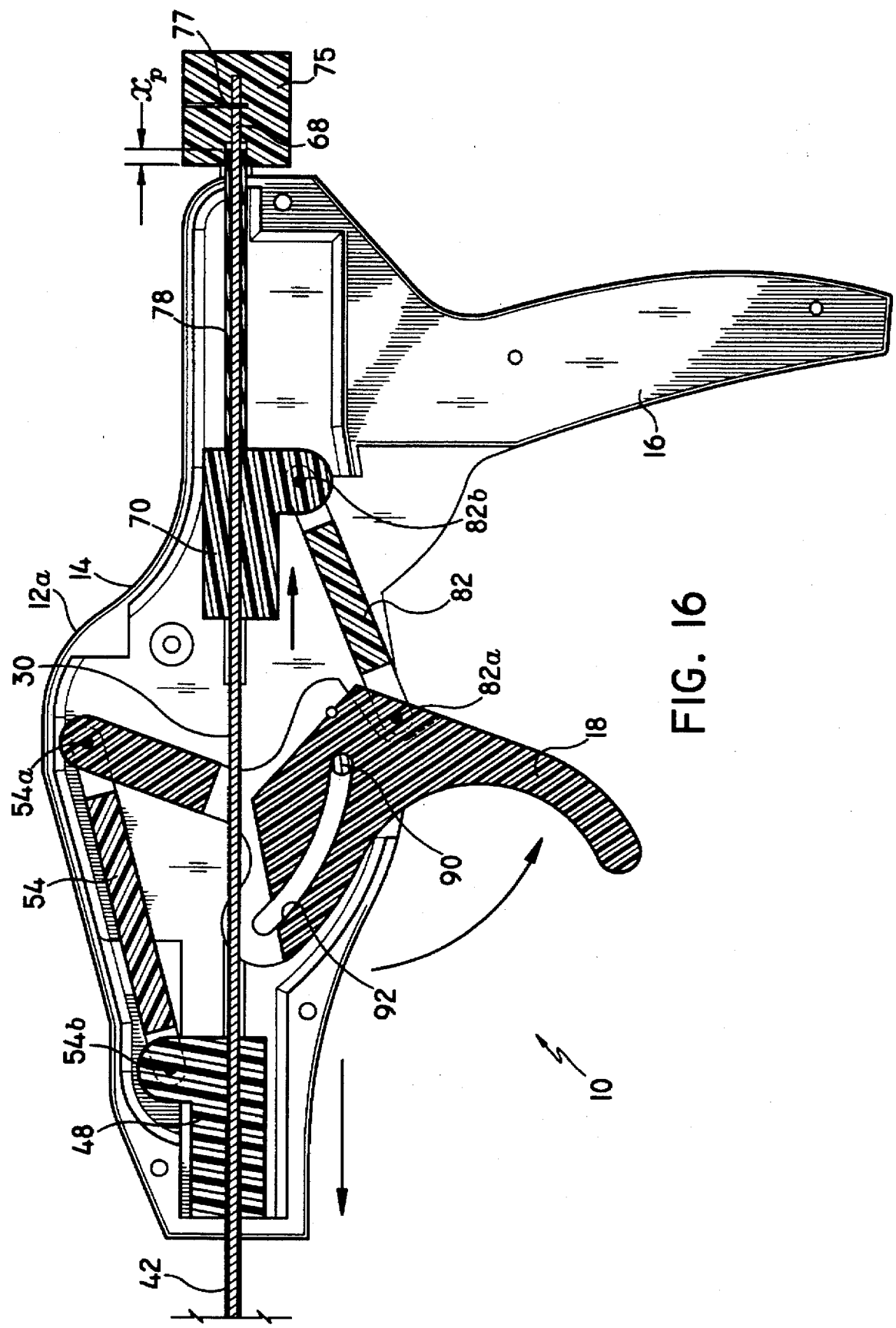
FIG. 16 is a side elevational view in cross-section of the handle portion of the surgical apparatus of FIG. 1 illustrating the relative orientation of the components associated therewith in positions corresponding to the clip advancement tube being advanced toward a distal position.

Referring back to FIG. 14, prior to the manipulation of actuation handle 18 through the first segment of its actuating stroke, the proximal end of release tube 78 is disposed slightly distal of the axial bore 75a of control knob 75. As shown in FIG. 16, however, during the manipulation of actuation handle 18 through the first segment of its actuating stroke, the proximal actuation block 70 and release tube 78 translate in a proximal direction through a distance "$x_p$" which is substantially less than the distance "$x_d$" through which the distal actuation block 48 travels during the same period of time. Consequently, during the first segment of the actuating stroke of actuation handle 18, the proximal end of release tube 78 translates only a short distance within the axial bore 75a of control knob 75, remaining free from contact with the proximal wall of axial bore 75a, and having no effect of the longitudinal position of control knob 75.

However, as illustrated in FIG. 21, once the distal actuation block 48 reaches its distal-most position, the pivot point of actuation handle 18 transfers from guide pin 90 to coupling pin 54a. As a result, the remaining portion of the actuating stroke of actuation handle 18 is guided by the interaction of guide pin 90 and the arcuate guide slot 92 formed in actuation handle 18. Consequently, further manipulation of actuation handle 18 toward stationary handle 16 urges proximal actuation block 70 in a proximal direction, driving release tube 78 proximally. As a consequence, control knob 75 is urged proximally, causing the release of engagement tabs 74a and 74b from the complementary notches formed at the proximal end of barrel portion 14, and effectuating the proximal withdrawal of control rod 68 relative to support tube 30. Accordingly, the arcuate expansion portions 62b and 64b of locator 60 are withdrawn into the axial bore 34a of support fixture 34, through the crescent shaped aperture 38 formed in the bail portion 26 of surgical clip 22.

Following the withdrawal of locator 60 into the axial bore 34a of support fixture 34, the distal end portion of the elongated body 20 of surgical apparatus 10 may be withdrawn from the surgical site. As best seen in FIG. 22, at the conclusion of the procedure, the opposed legs 24a and 24b of surgical clip 22 are securely engaged to the exterior wall of blood vessel 104 such that the hole once formed therein is closed, thereby preventing blood from flowing therethrough.

Although the subject invention has been described with respect to a preferred embodiment, it is apparent that changes may be made to the invention without departing from the spirit and scope of the invention as defined by the appended claims.

What is claimed is:

1. An apparatus for applying a surgical clip to an exterior wall of a blood vessel to at least partially close a hole formed therein comprising:

a) a handle portion;

b) an elongated body extending distally from the handle portion and dimensioned to extend through a hole in the wall of a blood vessel, and defining a longitudinal axis;

c) a collapsible locator operatively associated with the elongated body and moveable between a collapsed retracted position disposed within a distal end portion of the elongated body and an expanded deployed position extending from the distal end portion of the elongated body, the locator being adapted and configured to expand within an interior lumen of the blood vessel in the deployed position to maintain the distal end portion of the elongated body in a desired location with respect to the hole in the blood vessel wall; and d) a surgical clip releasably supported adjacent the distal end portion of the elongated body and having first and second opposed clip legs connected by a bail portion, the opposed clip legs dimensioned to span the hole in the blood vessel wall, the clip legs having distal engaging portions and being movable from an open position to a closed position, the distal engaging portions extending inwardly at an oblique angle relative to the longitudinal axis when in the closed position to engage the exterior surface of the blood vessel wall to at least partially close the hole formed therein when the locator is substantially in the deployed position.

2. An apparatus as recited in claim 1, wherein the locator has a generally loop-like configuration in the deployed position.

3. An apparatus as recited in claim 1, wherein at least a portion of the locator is formed from a material having shape memory characteristics.

4. An apparatus as recited in claim 1, wherein the the bail portion of the surgical clip has an aperture provided therein to accommodate movement of the locator from the deployed position to the retracted position upon application of the clip to the exterior wall of the blood vessel.

5. An apparatus as recited in claim 4, wherein a control rod extends from the handle portion through the elongated body and is mounted for movement between a proximal position and a distal position to effectuate the movement of the collapsible locator between the retracted position and the deployed position.

6. An apparatus as recited in claim 5, wherein a control knob is operatively mounted to a proximal end of the control rod to facilitate the longitudinal movement thereof.

7. An apparatus as recited in claim 6, wherein the control knob includes a pair of opposed locking tabs configured to releasably engage corresponding reception structure provided on a proximal end portion of the handle portion when the collapsible locator is disposed in the deployed position.

8. An apparatus as recited in claim 7, wherein the elongated body includes an outer tubular member, the tubular member moveable between a proximal position and a distal position.

9. An apparatus a recited in claim 8, wherein support structure is provided adjacent a distal end of the elongated body for releasably supporting the surgical clip.

10. An apparatus as recited in claim 9, wherein a pair of diametrically opposed ramps are formed adjacent a distal end of the elongated body distal of the clip support structure, the camming ramps causing the opposed arms of the surgical clip to move between a closed position and an open position in response to longitudinal movement of the outer tubular member from the proximal position toward the distal position.

11. An apparatus as recited in claim 10, wherein an actuation handle is operatively associated with the handle portion and is mounted for manipulation through an actuating stroke.

12. An apparatus as recited in claim 11, wherein movement of the actuation handle through a first segment of the actuating stroke causes the outer tubular member to move from the proximal position to the distal position, and movement of the actuation handle through a second segment of the actuating stroke causes the control rod to move from the distal position to the proximal position.

13. An apparatus as recited in claim 12, wherein movement of the actuation handle through the second segment of the actuating stroke releases the control knob from an engaged position.

14. An apparatus as recited in claim 13, wherein distal and proximal actuating members are supported with the handle portion and are operatively connected to the actuation handle, the distal actuating member connected to a proximal end of the outer tubular member and the proximal actuating member connected to a release tube which is dimensioned to interact with the control knob upon movement of the actuation handle through the second segment of the actuating stroke.

15. An apparatus as recited in claim 12, wherein a first control link connects the distal actuating member to the actuation handle and second control link connects the proximal actuating member to the actuation handle.

16. An apparatus for applying a surgical clip to an exterior wall of a blood vessel to at least partially close a hole formed therein comprising:

a) a handle portion;

b) an elongated body extending distally from the handle portion and dimensioned to extend through a hole in the wall of a blood vessel, the elongated body portion defining a longitudinal axis; and c) a collapsible locator operatively associated with a distal end portion of the elongated body and moveable between a collapsed retracted position and an expanded deployed position, the locator being adapted and configured to expand within an interior lumen of the blood vessel to maintain the distal end portion of the elongated body in a desired location with respect to the hole in the blood vessel wall, the locator having proximal engaging portions extending in a substantially transverse direction relative to the longitudinal axis of the elongated body to engage the interior wall surface of the blood vessel wall, such that a surgical clip releasably supported adjacent the distal end portion of the elongated body can be applied to the exterior wall of the blood vessel to at least partially close the hole formed therein when the locator is substantially in the deployed position.

17. An apparatus for applying a surgical clip to an exterior wall of a blood vessel to at least partially close a hole formed therein comprising:

a) a handle portion including an actuation handle mounted for movement through an actuating stroke;

b) an elongated body extending distally from the handle portion and dimensioned to extend through a hole in the wall of a blood vessel;

c) a collapsible locator loop operatively associated with the elongated body and moveable between a collapsed retracted position disposed within a distal end portion of the elongated body and an expanded deployed position extending from the distal end portion of the elongated body, the locator loop being adapted and configured to expand within an interior lumen of the blood vessel in the deployed position to maintain the distal end portion of the elongated body in a desired location with respect to the hole in the blood vessel wall;

d) a surgical clip releasably supported adjacent the distal end of the elongated body and configured for application to the exterior wall of the blood vessel to at least partially close the hole formed therein, the surgical clip having a pair of opposed clip legs connected by a bail portion, the bail portion having an aperture provided therein to accommodate movement of the locator loop between the deployed position and the retracted position; and e) an actuation assembly housed within the handle portion and operatively connected to the actuation handle such that movement of the actuation handle through a first segment of the actuating stroke effectuates longitudinal movement of the surgical clip toward the exterior wall of the blood vessel and movement of the actuation handle through a second segment of the actuating stroke effectuates movement of the collapsible locator loop from the deployed position to the retracted position.

18. An apparatus as recited in claim 17, wherein a control rod extends from the handle portion through the elongated body portion and is mounted for movement between a proximal position and a distal position to effectuate the movement of the collapsible locator loop between the retracted position and the deployed position.

19. An apparatus as recited in claim 18, wherein a control knob is operatively mounted to a proximal end of the control rod to facilitate the longitudinal movement thereof and includes means for releasably engaging the handle portion when the collapsible locator loop is disposed in the deployed position.

20. An apparatus as recited in claim 19, wherein the elongated body portion includes an outer tubular member mounted for axial movement with respect to the handle portion between a proximal position and a distal position.

21. An apparatus a recited in claim 20, wherein a pair of diametrically opposed camming ramps are formed adjacent a distal end of the elongated body, distal of the clip support position, the camming ramps causing the opposed legs of the surgical clip to move between a closed position and an open position in response to longitudinal movement of the outer tubular member from the distal position toward the proximal position.

22. An apparatus as recited in claim 21, wherein movement of the actuation handle through the first segment of the actuation stroke causes the outer tubular member to move from the proximal position to the distal position, and movement of the actuation handle through the second segment of the actuating stroke causes the control rod to move from the distal position to the proximal position.

23. An apparatus as recited in claim 22, wherein movement of the actuation handle through the second segment of the actuating stroke releases the control knob from an engaged position.

24. An apparatus as recited in claim 23, wherein the actuating assembly includes a distal actuating member connected to a proximal end of the outer tubular member and a proximal actuating member connected to a release tube which is dimensioned to interact with the actuator upon movement of the actuation handle through the second segment of the actuating stroke.

25. A method for applying a surgical clip to an exterior wall of a blood vessel to at least partially close a hole formed therein, comprising the steps of:

a) taking an elongated body having a surgical clip supported adjacent a distal end portion thereof;

b) extending the elongated body through a hole in the wall of a blood vessel such that at least a distal end portion thereof projects into an interior lumen of the blood vessel;

c) deploying a locator from the distal end portion of the elongated body into the interior lumen of the blood vessel such that the locator moves from a contracted position to an expanded position in engagement with interior wall portions of the blood vessel to maintain the elongated body in a desired position with respect to the hole in the wall of the blood vessel;

d) applying the surgical clip to an exterior wall portion of the blood vessel to at least partially close the hole therein; and e) retracting the locator from the interior lumen of the blood vessel.

26. A method according to claim 24, wherein the step of applying the surgical clip includes the step advancing the surgical clip in a distal direction from a proximal support position on the elongated body.

27. A method according to claim 26, wherein the step of advancing the surgical clip in a distal direction includes the step of moving the surgical clip between open and closed positions.

28. A method according to claim 25, wherein the step of deploying the locator includes the step of moving the locator from the collapsed position within the distal end portion of the elongated body to the expanded position extending from the distal end portion of the body.

29. A method according to claim 25, wherein the step of retracting the locator includes the step of withdrawing the locator through an aperture formed in a bail portion of the surgical clip.

30. A method according to claim 25 wherein the step of withdrawing the locator is concomitant with the step of applying the surgical clip to the exterior wall of the blood vessel.

31. A method according to claim 25, wherein the step of extending the elongated body through the hole in the wall of the blood vessel includes the step of extending the elongated body through a cannula inserted through the wall of the blood vessel.

32. A method according to claim 27, wherein the step of applying the surgical clip includes moving the surgical clip to the closed position whereby distal engaging portions of the surgical clip extend inwardly toward each other to engage the vessel wall portions.

33. A method for applying a surgical clip to an exterior wall of a blood vessel to at least partially close a hole formed therein comprising the steps of:

a) taking an elongated body having a surgical clip including a pair of opposed arms supported adjacent a distal end portion thereof;

b) extending the elongated body through the hole in the blood vessel wall such that at least a distal end portion thereof projects into an interior lumen of the blood vessel;

c) deploying a locator loop from the distal end portion of the elongated body into the interior lumen of the blood vessel to maintain the elongated body in a desired position with respect to the hole in the blood vessel wall;

d) causing the pair of opposed arms of the surgical clip to move between open and closed positions to effectuate application of the surgical clip to the vessel wall portions defining the hole to substantially close the hole by an inward bias of the arms of the surgical clip; and e) retracting the locator loop from the interior lumen of the blood vessel relative to the surgical clip.

34. A method according to claim 33, wherein the step of causing the opposed arms of the surgical clip to move between open and closed positions includes the step of advancing the surgical clip in a distal direction with respect to a pair of opposed camming ramps disposed adjacent the distal end of the elongated body.

* * * * *